United States Patent [19]

Scheicher

[11] 4,321,042
[45] Mar. 23, 1982

[54] CERAMIC DENTAL IMPLANT

[76] Inventor: Hans Scheicher, Rondell Neuwittelsbach 4, D 8000 Munich 19, Fed. Rep. of Germany

[21] Appl. No.: 235,401

[22] Filed: Feb. 18, 1981

Related U.S. Application Data

[63] Continuation of Ser. No. 778,284, Mar. 16, 1977, abandoned.

[30] Foreign Application Priority Data

Mar. 16, 1976 [SE] Sweden .................. 7603291

[51] Int. Cl.³ .............................. C09K 3/00
[52] U.S. Cl. ...................... 433/201; 106/35; 433/202; 433/212; 433/215
[58] Field of Search ............ 106/35; 433/201, 202, 433/212, 215

[56] References Cited

U.S. PATENT DOCUMENTS

| 3,069,773 | 12/1962 | Saffir | 32/8 |
| 3,090,094 | 5/1963 | Schwartzwalder et al. | 25/156 |
| 3,458,329 | 7/1969 | Owens et al. | 106/39.5 |
| 3,488,847 | 1/1970 | Pettrow | 32/8 |
| 3,934,347 | 1/1976 | Lash et al. | 32/10 A |

FOREIGN PATENT DOCUMENTS

| 477144 | 4/1975 | Australia . |
| 480554 | 4/1975 | Australia . |
| 990126 | 4/1965 | United Kingdom . |
| 1323229 | 7/1973 | United Kingdom . |

Primary Examiner—Lorenzo B. Hayes
Attorney, Agent, or Firm—Sughrue, Mion, Zinn, Macpeak and Seas

[57] ABSTRACT

A dental implant having a sintered and porous surface and comprising a biocompatible ceramic matrix and, intermixed therein, inorganic fibers.

15 Claims, 4 Drawing Figures

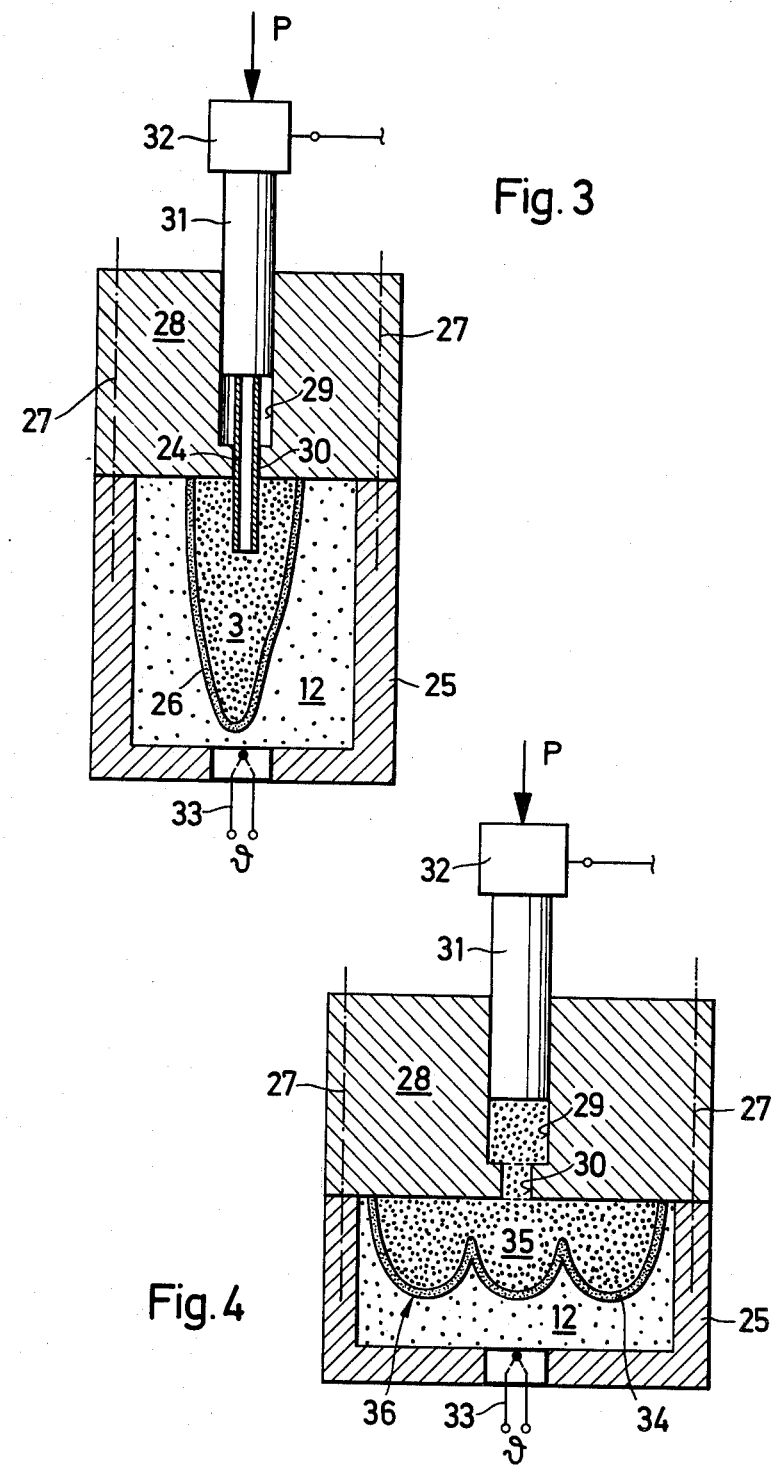

CERAMIC DENTAL IMPLANT

This is a Continuation, of application Ser. No. 778,284, filed Mar. 16, 1977 now abandoned.

The invention concerns ceramic substances, in particular their composition, method for the production of ceramic substances and processing of same, as well as products which contain these ceramic substances, in particular prosthetic elements, method for their production and use, as well as associated techniques.

The ceramic substances according to the invention are particularly suitable for the production of prosthetic elements, chiefly those which can be used in the body, whereby they are suited especially for dental implants. The ceramic substances according to the invention are characterized by a mixture of a ceramic base substance and fine inorganic fibers, whose melting temperature is higher than the sintering temperature of the ceramic base substance. When manufacturing ceramic substances according to the invention care is taken that the ceramic base substance, in the molten form that it takes on during sintering, does not dissolve the fibers as such.

By fine fibers in this specification, fibers or filaments and wires having a diameter less than about 0,6 mm are understood.

The fibers according to the invention can be present in the ceramic base substance matrix in the form of whiskers, filaments, staple fibers, chopped fibers, threads, chopped strands as well as further processed products such as slubbings, rovings, netting, matting, fibrous webs, bonded fibrous materials, felts and woven materials. Usually it suffices to have the fibers in short pieces, of lengths approximately 0,1–60 mm, preferably about 0,5–30 mm, in the ceramic base substance.

For the production of porous ceramic bodies, fibers in pieces of about 0,5– about 3 mm are particularly suitable. An adequately uniform distribution of the fibers in the base substances is generally sufficient to ensure that the ceramics manufactured from the substances have the desired rigidity. This applies especially for the production of porous ceramic bodies having surfaces not prone to rejection by the tissues and which enable adherence and ingrowth of bone tissue. These porous bodies contain a large number of vesicular cavities merging partly into one another like a sponge. The pores vary in diameter from the smallest pore of diameter less than 1 $\mu$m to pores with a diameter of over 500 $\mu$m, whereby in a piece of ceramic pores of different sizes are evident. Pores of diameter from about 10 $\mu$m to about 400 $\mu$m are preferred. The average value of the pore diameter should be approximately 100–200 $\mu$m, whilst the quantity of pores having a diameter larger than 300 $\mu$m should not account for more than 10%, preferably 5%. In the porous bodies the pores take up a volume of about 10% to about 90% with respect to the total volume. Proportions of pores from about 20 Vol.% to about 30 Vol.% are especially suited for use as adhering layer for the ingrowth of tissue.

It is on the other hand also possible to considerably increase the rigidity of the baked materials obtained from the ceramic substances, and to manufacture so-called fiber-reinforced high strength composite materials, by means of orientating the fibers in the matrix, preferably at angles of about 90° to the maximum load and approximately parallel to one another, this being rendered possible by use of fibers in one of the above-mentioned forms.

Conventional organic fibers prove unsuitable for the production of the substances according to the invention since their melting points are lower than the temperatures necessary for the sintering together of the ceramic base substances, the temperatures for the ceramic base substances used lying in a region from about 630°–1900° C. The composition of the ceramic base substances used within the frame of the invention at hand will be subsequently dealt with in more detail.

In the following a series of fibers are indicated, though not claiming entirety, which are suitable for the manufacture of ceramic substances as according to the invention. They are as follows:

Pure quartz fibers from 99.99% silicon dioxide, which on account of their high thermal and chemical stability present no problems when used for implants.

Carbon fibers, which in the purest form are referred to as graphite fibers and are relatively economical to manufacture. When using carbon fibers it must be remembered that although they present no physiological problems, the material exhibits a high heat conduction capacity and a high electricity conduction capacity.

The processing of carbon fibers should be carried out in a vacuum in order to prevent oxidation.

Metal filaments, manufactured by heat-drawing with or without sheathing and by pressing out of the melt through narrow nozzle openings and subsequent solidification, or by the so-called Taylor Process. Metal filaments with a diameter equal to or larger than 100 $\mu$m can, according to DIN 60001 E be referred to as wires. When metal filaments or wires make up the fiber content in the ceramic substances according to the invention and these substances are used for implants, care should be taken to use a ceramic base substance which, when molten, wets the metal filaments well, so that after solidification of the ceramic substance these are not bare. Otherwise they could be attacked by the body fluids, which dissolve the metals and could lead to so-called "metallosis" i.e. poisoning by metal ions. The danger of such a metallosis is not great even if the metal filaments are not completely covered by the ceramic base substance, since the fibers account for only a small percentage of the total material and are furthermore embedded for the most part in the matrix of the ceramic base substance. Since however there are other fibers where the danger of metallosis can from the start be excluded, ceramic substances containing metal filaments as fiber content are generally not used for the outer layer of prosthetic elements but rather as reinforced core substances, these being covered by the overlying layers. Examples of metal fibers would be steel fibers, fibers of René 41 (a nickel-based alloy), niobium fibers, molybdenum fibers and tungsten fibers.

Filaments with a tungsten core, that is, reinforcing elements which are manufactured by making the actual reinforcing material on a tungsten core of, for ex., about 12 $\mu$m. To these belong in particular boron threads, (diameter approximately 90–150 $\mu$m) which can be additionally coated with silicon carbide to a thickness of about 4 $\mu$m, or whose surface is treated with a nitration. Boron carbide filaments with a tungsten core, silicon carbide filaments (diameter approximately 100 $\mu$m) with a tungsten core and titanium dioxide filaments with a tungsten core also belong to this group. A disadvantage of the last-mentioned threads lies in that they are relatively thick.

Synthetic ceramic fibers: i.e. synthetic fibers of borides, carbides, nitrides, oxides, silicides and/or silicates.

To these belong in particular: boron carbide fibers, boron nitrate fibers and zirconium silicate fibers, which are very fine, as well as the coarser zirconium dioxide fibers and in particular the somewhat thicker aluminium oxide fibers; also the so-called Mullit fibers which comprise for the most part aluminium oxide. The ceramic fibers, as opposed to the metal fibers, have the advantage that when using the ceramic substances according to the invention for the production of prosthetic elements, there is no danger of metallosis or electrolytic disturbances. Basalt as well as kaolin fibers are also suitable.

Details concerning the manufacture and the properties of the above-described fibers can be taken from a brochure on "Faserverstärkte Hochleistungs-Verbundwerkstoffe" by Rainer Taprogge, Rolf Scharwächter, Peter Hahnel, Hans-Joachim Müller and Peter Steinmann, of the Institut zur Erforschung technologischer Entwicklungslinien ITE.

A further group of fibers which is particularly suitable for the manufacture of the ceramic substances according to the invention are the so-called whiskers. Whiskers are discontinuous fiber-like single crystals with exceptionally high tensile strength and modulus of elasticity, which however are at present relatively expensive. But since only small quantities of the whiskers are required for the ceramic substances according to the invention their use is also economically feasible. Whiskers suitable for the ceramic substances according to the invention include in particular beryllium oxide whisker, boron carbide whisker, graphite whisker, magnesium oxide whisker, aluminium nitrite whisker, silicon nitrite whisker as well as in particular aluminium oxide—that is, sapphire whisker and silicon carbide whisker. Silicon carbide whiskers occur in two modifications, the so-called α-silicon carbide whisker and the so-called β-silicon carbide whisker. The α-silicon carbide whiskers are hexagonally-centered, in diameter about 10 μm to about 100 μm, and in length about 1 to about 60 mm. The β-silicon carbide whiskers are cubic, having diameters of about 0,5 μm to about 3 μm, and lengths of about 1 to about 30 mm. Precisely these β-silicon carbide whiskers are excellently suited for embedding in dental ceramic base substances. Besides the above-mentioned whiskers, metallic whiskers such as, for example, chrome whiskers, cobalt whiskers and nickel whiskers, conditionally also copper- and silver whiskers, can also be used in ways according to the invention. The same applies also for the so-called Schadlitz whiskers, these being polycrystalline metallic threads. The above-mentioned metallic whiskers are all likewise subject to the disadvantage already mentioned in connection with metal filaments, namely that when not completely covered by the matrix of the ceramic base substance they can, on coming into contact with body liquids, be the source of possible metallosis and electrolytic disturbances, if the ceramic substances produced from them and the corresponding base substances are used for implants.

Details concerning the above-mentioned whiskers, especially as to their manufacture and their properties, can be taken from the previously-mentioned brochure on "Faserverstärkte Hochleistungs-Verbundwerkstoffe". With respect to the silicon carbide whiskers attention is drawn also to an article by A. Lipp in the journal "Feinwerktechnik" 74. year 1970, issue number 4, pages 150–154. Details concerning polycrystalline metallic whiskers or metallic threads can be taken from articles by Hermann J. Schadlitz, published in "Fachberichte für Oberflächentechnik" 8. year 1970, issue number 7,8, pages 145–150 and "Zeitschrift für Metallkunde" Band 59/1968, issue number 1, pages 18–22.

Generally one uses in each case one type of fiber in one ceramic base substance. In principle however, also mixtures of differnet fibers can be used in one ceramic base substance. As base substances, which are mixed with the above-mentioned fibers together with the ceramic substances according to the invention, conventional ceramic substances intended as bone substitute, particularly glass-ceramic and the familiar dental-ceramic substances like normal dental ceramic, metal ceramic and hard ceramic, as well as aluminium oxide ceramic substances can be used. As base substances one can use in particular so-called core substances i.e. porcelain substances which are used in a conventional way for the inner makeup of artificial teeth and so-called dentine substances i.e. porcelains which should replace the dentine in the natural tooth. So far as the base substance—this applies for core- and dentine substances—are normal dental-ceramic substances, they contain mixtures of quarz, kaolin, and feldspar. Typical examples of such base substances contain 70–90 parts by weight feldspar, especially orthoclase-potassiumfeldspar, about 0,5 to 15 parts by weight—preferably 1 to 10 parts by weight—kaolin, and about 0,5 to 25 parts by weight—preferably about 1 to 18 parts by wt.-quarz, as well as about 0 to 2 parts by wt.—preferably 0 to 1,3 parts by wt.—pigments and opaques. Instead of the quarz, various allotropic silicon compounds such as, for example, cristobalite, can be used, this serving in particular to regulate the thermal coefficient of expansion. An increase in the proportion of silicon increases the power of resistance. Other base substances contain in place of the feldspar nepheline syenite, a mineral made up of approximately 50% sodium feldspar, (albite) 25% potassium feldspar (microlite), and 25% nephelite. In the case of the dentine base substances the silicon content can be raised to about 20 parts by wt. In the base substances the silicon content can be wholly or partly replaced by aluminium oxide. If the aluminium oxide content is raised, for example to 60 and 70 parts by wt., then base substances are obtained which can be classified with the familiar hard-porcelains and can also be referred to as aluminium oxide ceramic substances. One can however also use the so-called enamel substances as base substances, these serving as enamel layer for artificial teeth and porcelain crowns.

The base substances can further contain various fluxes, such as, for example, lithium and potassium silicate which effect alterations in the firing temperature or the thermal coefficient of expansion. The addition of a flux enables adaptation of the base substances to the thermal coefficient of expansion of metals or hard ceramics, so that these base substances can be fired onto profile parts, cores, inserts or superstructures of these materials. One differentiates accordingly between metal-ceramic and hard-ceramic substances. As examples of aluminium oxide ceramic substances the Vitadur and Vitadur-S-ceramic substances can be mentioned, which come as core substances, dentine substances and as enamel substances, and which are manufactured by the Vita Zahnfabrik Säckingen in West Germany. Relevant details can be taken from the brochure "Die Vitadur-Technik" Nr. 11/73-500 of the Vita Zahnfabrik, Säckingen, Germany. Examples of metal ceramic substances are described in the DT-AS No. 1 441 346, to which reference is here made. As further examples of metal-ceramic substances the Biodentdentine and the Biodent core substances of the firm De Trey Gesellschaft D 6200 Wiesbaden as well as the Vita-VMK substances of the Vita Zahnfabrik, Säckingen, Germany and the Vivodent-PE-ceramic substances of the firm Ivoclar AG FL-9494 Schaan/Lichtenstein can be mentioned. i.e. of ceramic substances which can be fired onto $Al_2O_3$ cores.

An example of a metal-ceramic base substance sintering at a firing temperature of 900° C. has the following composition:

| Component | Percent | Component | Percent |
| --- | --- | --- | --- |
| $SiO_2$ | 65,518 | $Li_2O$ | 1,236 |
| $Al_2O_3$ | 14,078 | CaO | 1,778 |
| $K_2O$ | 9,552 | MgO | 1,202 |
| $Na_2O$ | 6,636 | | |

Examples of glass ceramic base substances are the pyrex glass from the GCC Company in Japan and Vycor glass from the Dentists Supply Company in the U.S.A.

The DT-AS No. 2 326 100 describes a glass ceramic base substance with apatite crystal phase, which can likewise be used for the manufacture of substances according to the invention. The DT-OS No. 2 238 263 and the DT-OS No. 2238263 describe a further example for ceramic base substances. The abovementioned ceramic substances are for the most part not porcelains according to the classical description—i.e. not mixtures of quarz, feldspar and kaolin, but porcelain products attaining to a different concept which, with respect to their composition, molding and firing do not resemble normal porcelain in any way. With regard to their terminology attention is drawn in particular to an article by Dr. Walter Pralow, Säckingen, in the journal "Das Dental Labor", issue number 2/1969, pages 66 and foll. The adoption of the expression "Ceramic substances" for these substances too arises from the fact that these substances are prepared according to ceramic methods, although as far as their composition is concerned, they resemble more the glasses. Substances are preferably used whose firing temperatures lie in the region of 900° to 1400° C., preferably 900°–1200° C.

The melting temperatures of the threads must be higher than the sintering temperature of the base substances used in conjunction with them, this temperature difference amounting to some thousand degrees Celsius, for example to about 3100° Celsius. The temperature differences are preferably 400° C. or more.

The fibers used are preferably of lengths from about 0,1 to 60 mm, whereby lengths from about 0,5 mm to about 30 mm are particularly preferred. Fibers of lengths from 0,5 mm to about 3 mm are particularly suitable for the production of porous bodies, preferably for the dental region.

The thickness of the fibers employed reaches as a maximum to about 600 $\mu$m, whereby fibers of thickness from about 0,5 $\mu$m to about 100 $\mu$m are preferred. For the manufacture of dental ceramic substances which are applied as the outer layer on implants, whiskers of thickness from about 0,5 $\mu$m to about 20 $\mu$m have proved suitable, thicknesses to about 10 $\mu$m being especially favourable. The best results to date were obtained with $\beta$-silicon carbide whiskers, these having a thickness of about 0,6 to 3 $\mu$m.

Very good results were obtained with basalt threads of thickness about 6 $\mu$m in lengths about 1-3 mm, and carbon fibers with a thickness of about 10 $\mu$m and lengths from about 0,5 mm to about 1,5 mm.

In order to obtain the desired reinforcement in the material at least 5 Vol.% of fibers, with reference to the base substance in not-yet-processed powder form, should be added.

For the formation of a layer permeated by vacuoles, on the other hand, this enabling an easier ingrowth of bone substance, relatively small additions of fibers to the ceramic base substances suffice. Experiments have shown that a fiber Vol.% of 0,01 to 0,02 relative to the ceramic base substance in unprocessed powder condition can be adequate.

For the formation of the layer permeated by vacuoles, the fibers with up to 5 wt.%—relative to the weight of the ceramic base substance in not-yet-processed powder form—are added preferably in a ratio of about 0,01 to about 2 wt.% whereby with quantities from about 0,02–0,05 wt.% excellent results are obtained.

When however, the ceramic substances should serve as reinforced composite material, an addition of 5 wt.% to 50 wt.% is recommended, preferably 10 wt.% to 25 wt.% relative to the weight of the ceramic base substance in not-yet-processed powder form.

Introduction of the very finely-divided metallic silver into the ceramic substance can be effected as follows:

To any one of the above-described ceramic base substances—preferably a dentine substance such as, for example, a Vitadur-dentine substance—a silver salt having anions easily decomposed by heat or an easily reducible silver salt is added in quantities from about 1 to about 50 wt.%, preferably about 5 to about 30 wt.% relative to the ceramic base substance, and is uniformly mixed with the ceramic base substance, the salts preferably being in solution.

Silver salts from organic acids are especially suitable, as for example silver oxalate, silver acetate, and silver tartrate. Also silver nitricum, i.e. silver nitrate, is suitable here. The silver salts mixed with the base substances are subsequently decomposed.

This is possible by warming above the relevant decomposition temperature. With this procedure however great care must be taken since—as for example with silver nitrate—poisonous fumes can result which must be very carefully led off. In order to avoid endangering the personnel with fumes of this sort the decomposition is accordingly carried out preferably by a chemical reduction. The mixture of silver salts and base substances is hereby mixed with a reducing agent, as they are used for example in photography, being referred to as "Developer". Examples of such reducing agents or developers are androquinone, hydroquinone, pyrocatechin, ortho- and meta- amino phenols, such as metol (para-n-methamino-phenol); glycin (4-hydroxy-phenylamino acetic acid); phenidon (1-phenyl-pyracolidon 3) hydrazone; hydrophosphorous acid $H_3PO_2$; dithionate ($Na_2S_2O_4$) as well as in particular formalin, aldehydes such as formaldehyde, acetaldehyde, propionaldehyde and also ascorbic acid and glucose. By premixing the mixture of the relevant ceramic substance and the relevant silver salt with the solution of such a developer, metallic silver is made to precipitate out from the silver salt. The product is subsequently washed several times with distilled water. When using formalin, acetaldehyde, propionaldehyde, ascorbic acid and glucose as reducing agent the repeated washing can be omitted due to their good compatibility under different conditions. The product is then dried and ground in a mortar, after which it can as ceramic base substance be further processed—as described before—and with fibers mixed into it or not. In the following an example is cited for the introduction of very finely-divided metallic silver into a base substance: 1 g of silver nitrate and 10 ml of distilled water are introduced into a flask. Through shaking the silver nitrate is dissolved. Then 10 g of a Vitadur-dentine base substance are added, as well as 20 ml of a normal commercial hydroquinone developer. The mixture is shaken carefully. The flask is subsequently filled with distilled water and the product allowed to settle. The liquid is then decanted, and the residue washed by repeated filling with, shaking and decanting of distilled water. The solid matter at the bottom of the flask is then dried. The dried product is ground in a mortar. It can then as previously described be further processed, for example by means of cocoa butter and with addition of a corresponding quantity of the previously-mentioned inorganic fibers.

The ceramic substances according to the invention have the advantage that they can be prepared according to need without great outlay on apparatus, for example in smaller dental-ceramic laboratories with which also individual dentists can be equipped. The ceramic substances according to the invention consequently exhibit a marked improvement in the field of prosthetic dentistry, since hereby, as becomes more apparent from the following details, a simple and quick production of direct implants pertaining in shape to the normal teeth and at the same time not being rejected by the tissues is possible. The use of these direct implants also prevents atrophy of the jaw, occurring until now in each case in the region of the extracted teeth. The use of such direct implants is thus not only for aesthetis reasons but also on medical grounds a considerable advance. The ceramic substances according to the invention are naturally not limited to the dental field, but can be used also for all other bone and joint implants as well as for cardiac valve substitutes. These prosthetic elements are only provided with a porous layer in those areas where ingrowth or adherence of the bone tissue onto the element is desired.

The ceramic substances according to the invention can, according to the requirements in each case, be mixed afresh from the fibers and a corresponding base substance by the technician responsible. In this case it is advantageous if the fibers can be supplied in packaged quantities.

In many cases however it is preferable if the ceramic substances are provided already mixed, and need only be opened and fired. With a number of fibers which don't exhibit any large surface energies and don't have a tendency to form bundles, it is sufficient to mix the fibers of the corresponding lengths and thicknesses with the relevant quantitiy of powdered ceramic base substance. In the case of other fibers however, this is not immediately possible, since these, on account of large surface energies, are held together in balls or bundles, this making a uniform mixing with the ceramic base substances difficult. This is the case particularly with, for ex. basalt fibers, carbon fibers and whiskers, whereby especially with $\beta$-silicon carbide whiskers separation problems occur. In these cases the fibers are brought into contact with a liquid or solid medium becoming volatile below the sintering temperature of the ceramic base substances, this medium exhibiting a surface energy which enables or effects separation of the fibers. For this such media are preferably used which solidify at room temperature and which are liquid at somewhat higher temperatures. The separation of the fibers occurs through the fibers being mixed with the liquid or liquefied medium. Examples of such media suited for the separation of fibers are synthetic materials, synthetic resins, waxes as well as glycerine, or cocoa butter, which have proved successful particularly for the separation of $\beta$-silicon carbide whiskers, basalt fibers and carbon fibers.

The ceramic base substances can be stirred in either after this, or just immediately before the processing of the ceramic substances, for which purpose the medium bringing about the separation is warmed again above its solidification point. When cocoa butter is used for separation of the fibers and kneading of the ceramic substances, it is added in quantities of about 10–100 wt.%, preferably about 40–80 wt.% relative to the ceramic substances according to the invention of fibers and base substances. It is particularly useful to decant the ceramic substances after their preparation into small containers, for example in mixing capsules, and to let them solidify in these. For the processing of the ceramic substances, the same are then warmed up in their containers so that they can subsequently be immediately opened and processed.

When the ceramic substances according to the invention are produced by a single mixture of the base substances with fibers having no tendency to form bundles, they are further processed as follows:

The ceramic substances are premixed with a modelling liquid which can be the same one as employed for mixing the ceramics used as base substances. The quantity of the modelling—or respectively mixing liquid amounts to about 5–10 wt.% relative to the quantity of the ceramic substance. Possible excesses of the mixing liquid are drawn off, for example by means of blotting paper. Distilled water is particularly suitable as a mixing liquid. Subsequently the dough-like ceramic substances are introduced into a mold, or compression mold, whose shape corresponds to that desired for the end product after the firing, for example a dental implant or a bone implant. Through shaking or such methods the ceramic substances are adequately consolidated, preventing the appearance of undesired large cavities during the firing and ensuring that the model is in each case perfectly shaped. The ceramic substances can also be fired onto a substrate. In this case they are applied in the desired layer thickness.

If the ceramic substances according to the invention contain fibers with a tendency to form bundles and are mixed with the corresponding base substances by means of the previously described volatile medium exhibiting a high surface energy, or if non-bundle-forming fibers are mixed with these media, preferably with cocoa butter which is preferred since this cocoa butter, on heating, doesn't boil but just sublimes directly, then before introducing the mass into the mold or applying onto a substrate it must be heated above the melting point of the medium.

When firing so-prepared ceramic substances according to the invention a muffle furnace or another corresponding furnance or a hot press containing the ceramic substances according to the invention is heated firstly to a temperature lower than the sintering temperature of the base substances used in the ceramic substances but which however is high enough to cause the medium bringing about a separation of the fibers, or the mixing fluid, to evaporate or sublime. This temperature is preferably selected lying between about 400° C. and about 600° C., usually about 500° C. This temperature is maintained long enough to confirm that the mixing liquid or the medium bringing about a separation of the fibers has completely evaporated or sublimed. This can be determined for the individual media by simple experiments, whereby one carries out the procedure over various time intervals, letting the substances subsequently become cold and then determining the proportion of the medium by analysis. This pre-firing takes as a rule about half an hour. After this the temperature in the furnace is raised to the firing temperature of the base substances used in the ceramic substances in each case. These temperatures are in the case of normal commercial ceramic substances, which are as a rule used for the base substances in each case indicated. In the case of other base substances they are determined by simple experimental series, whereby the firing temperature for different samples is raised step-wise by a few degrees Celsius. When the desired temperature in the interior of the ceramic substances according to the invention has been reached, this temperature is maintained for the normal firing time for firing of the corresponding base substances—i.e. for the time intervals ranging between 2 and about 30 minutes, preferably about 6 to about 10 minutes. After a further quarter of an hour the furnace is opened and the fired substance in the mold is removed, if necessary after a further cooling period in the furnace.

For the ceramic base substances so-called core substances can be used and be mixed with the corresponding fibers, in particular whiskers in orientated state, whereby in these cases the resulting ceramic material according to the invention comes into use preferably as core substance for the manufacture of dental implants or for the making of ball joints in joint prosthetics. In this case the admixture of fibers is selected to be greater than 5 wt.% or 5 vol.%, but however less than 50 wt.%/respectively 50 vol.%, relevant in each case to the base substance, so that a high rigidity is attained in the ceramics produced.

Particular advantages are evident however from the use of ceramic substances according to the invention when these are fired as an outer layer onto the implant, forming respectively a periosteum—or dental periosteum substitute. The ceramic base substance can here be either a core substance, a dentine substance or an enamel substance, its specific composition being dependent on whether the implant is to be made as metal-ceramic or as hard-ceramic. The implants exhibit in this case, from the outside to the inside, the following layering possibilities:

(a) dentine substance with fibers fired on a core substance without fibers.

(b) dentine substance with fibers fired on a dentine substance without fibers, which in turn in given cases is fired on a core substance.

(c) core substance with fibers, fired on a core substance without fibers.

(d) enamel substance with fibers, fired on a dentine substance and/or a core substance without fibers.

When the ceramic substances according to the invention form the outermost layer of a bone or dental root implant as bone periosteum-or dental root periosteum substitute, it is applied as appropriate in thichnesses of about 0.1 mm to about 5 mm, preferably in thicknesses of about 0.1 mm to about 1 mm. For dental implants the optimal thickness is about 0.3 to 0.5 mm. The desired vacuoles in this layer, which allow for the ingrowth of tissue, are formed during firing of the ceramic substances according to the invention, provided this doesn't occur under high pressure—i.e. in a vacuum about 5–50 mm Hg, preferably 10–20 mm Hg, under atmospheric pressure and with small excess pressures of up to approximately 1 kp/cm². In the case of low concentrations of fibers in the base substance—i.e. a proportion of fibers between about 0.01 to anout 1 wt.%, excess pressures of about 0.1 kp/cm² to about 0.5 kp/cm² give good results. These pressures are in fact sufficient to counterbalance the shrinkage of the substances during firing in a mold and to guarantee a complete formation, including details, of the implant without the pores being pressed in, since the ceramic substances are viscous at the sintering temperature. The pressure can be exerted on the ceramic substances during the whole firing process, this being so arranged, for example, by situating the whole firing chamber under a corresponding excess pressure. Normally however the pressure is first exerted after reaching the sintering temperature when the ceramic substances according to the invention are already viscous. We have here therefore a case of post-pressurizing. Examples for possible procedures of exerting a post-pressure are described by means of the FIGS. 1–4.

With higher proportions of fibers pressures higher than 1 kp/cm² are necessary in order to avoid the pores of the fired product becoming too large and the product brittle. If the fibers are metallic fibers, the firing is carried out in a vacuum or in the presence of a protective gas in order to prevent oxidation. As protective gases the noble gases are particularly suitable i.e. Helium, Argon, Krypton and Xenon, Argon being here the most preferred. If the firing occurs in sealed containers however, this precaution can, under certain conditions, be dispensed with. The size and number of the vacuoles, that is the porosity of the periosteum substitute layer produced from the ceramic substance according to the invention, can be regulated through the respective addition of fibers to the ceramic base substance. The most suitable mixtures within the given values can be determined for the individual fibers by simple experiments. When the vacuoles measure about 10 μm in diameter to about 300 μm in diameter and/or in depth, a good ingrowth into the implant in the bone tissue is to be expected, i.e. the new-forming bone tissue grows into the vacuoles and creates a firm contact between bone and implant. One can observe this from X-Rays taken at time-intervals of several weeks. The previously-given values are to be understood as average values. Besides the vacuoles of the given size a large number of small and very small vacuoles can be in evidence. Also the existence of single somewhat larger vacuoles doesn't matter.

When during sintering, the ceramic substances according to the invention are strongly pressure-compacted, i.e. with pressures over 1 kp/cm² and over, the occurrence of vacuoles can be reduced and finally prevented. Substances of this sort, being preferably manufactured together with core substances as ceramic base substances, are particularly suitable for the inner structure of the implants due to the very high degree of rigidity. In order to attain a good homogeneity very high pressures are necessary, lying for example in the region between about 10,000 kp/cm² and about 25,000 kp/cm². These pressures are preferably exerted as post pressures.

For these ceramics designed for load it is particularly advantageous and in some cases essential, that the fibers in the ceramic substance are orientated. Orientation of the fibers in the ceramic substance is relatively difficult to achieve. In some cases a practicable orientation can be attained by means of the medium effecting separation of the fibers, when this has a suitable surface energy. An orientation can also be achieved by means of familiar gravimetric or/and flow methods. In the case of metallic fibers an orientation can be effected by means of an electromagnetic field. A further possibility for orientation of the fibers is to introduce them in form of netting, matting, or woven material (or in form of fibrous webs, bonded fibrous material or felts, if it is not dependent on a particular geometrical orientation and need only be ascertained that in certain areas of the ceramic a larger but uniform distribution of fibers is present.)

According to a further refinement of the invention, ceramic substances with orientated fibers can be attained through the forming of the ceramic substances according to the invention into band- or plate-like strips by means of the medium effecting separation of the fibers, these strips being wound layerwise around a core. This occurs preferably using heated rollers, by means of which already part of the medium separating the fibers is driven off.

The ceramic substances according to the invention can be used for the production of bone implants of every sort. They are however particularly suitable for dental prosthetic elements. Here, apart from the already-described possibilities of application, whereby they essentially form the periosteum or dental periosteum of implants, they can also be used for making crowns, inlays, onlays or bridge constructions, there especially in pressure-compacted form whereby they constitute a rigid and resistant support for a dentine- and/or an enamel substance. These dental prosthetic elements can, together with natural and synthetic roots as well as with metallic and plastic constructions, be used for bridges.

In the following the invention is described in detail by means of the accompanying drawings for the case of dental ceramic substances and dental implants, as well as dental root implants. Naturally the techniques described in this special connection can also be used for making other bone-like implants.

FIG. 3 shows a further variation of the porcelain press technique shown in FIG. 2.

FIG. 4 shows the production of a multi-membered bridge from a fiber-reinforced material following a further variation of the porcelain press technique according to the invention.

Figure 1:
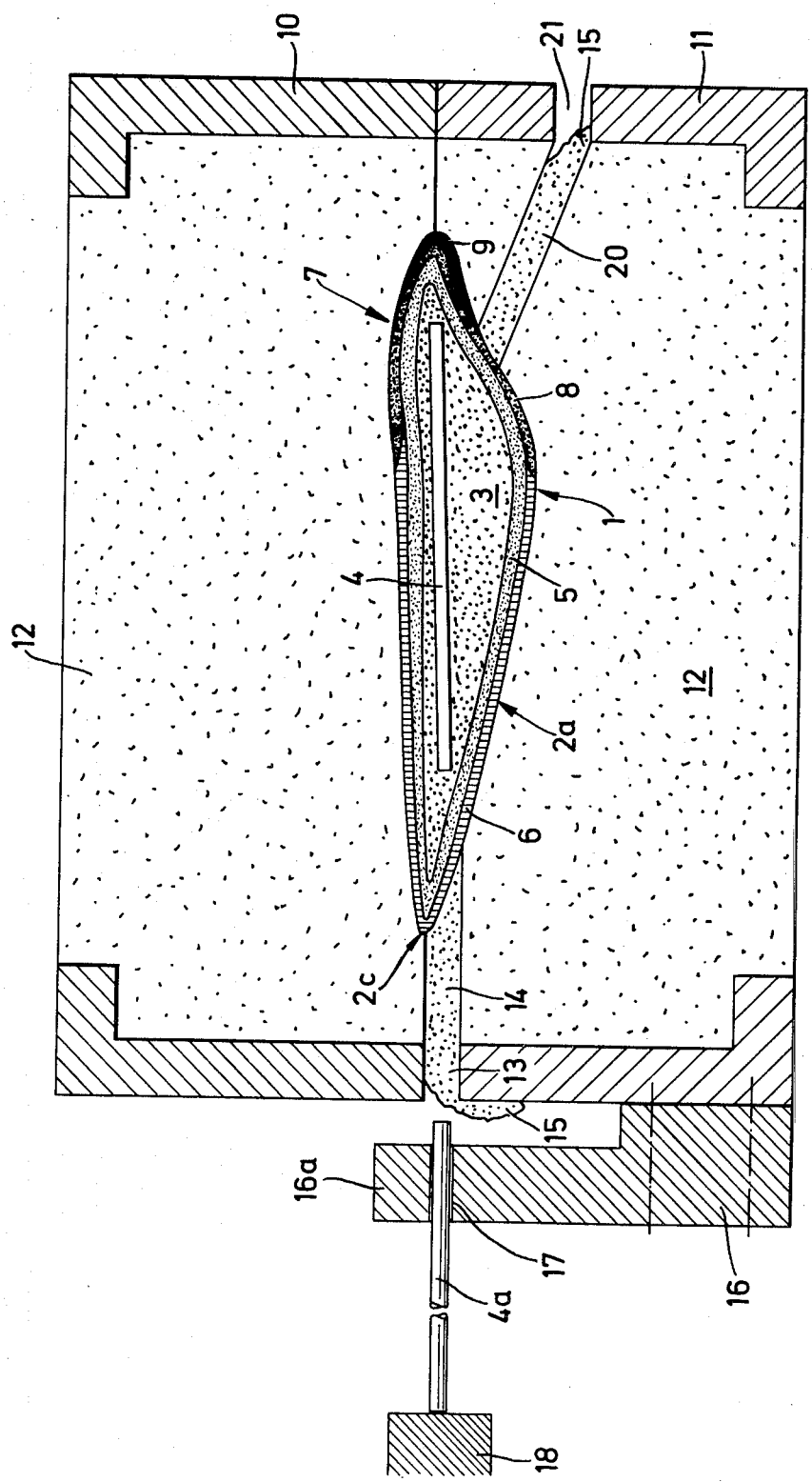
FIG. 1 shows a dental implant according to the invention and its production by means of a special porcelain press technique according to the invention.
Figure 2:
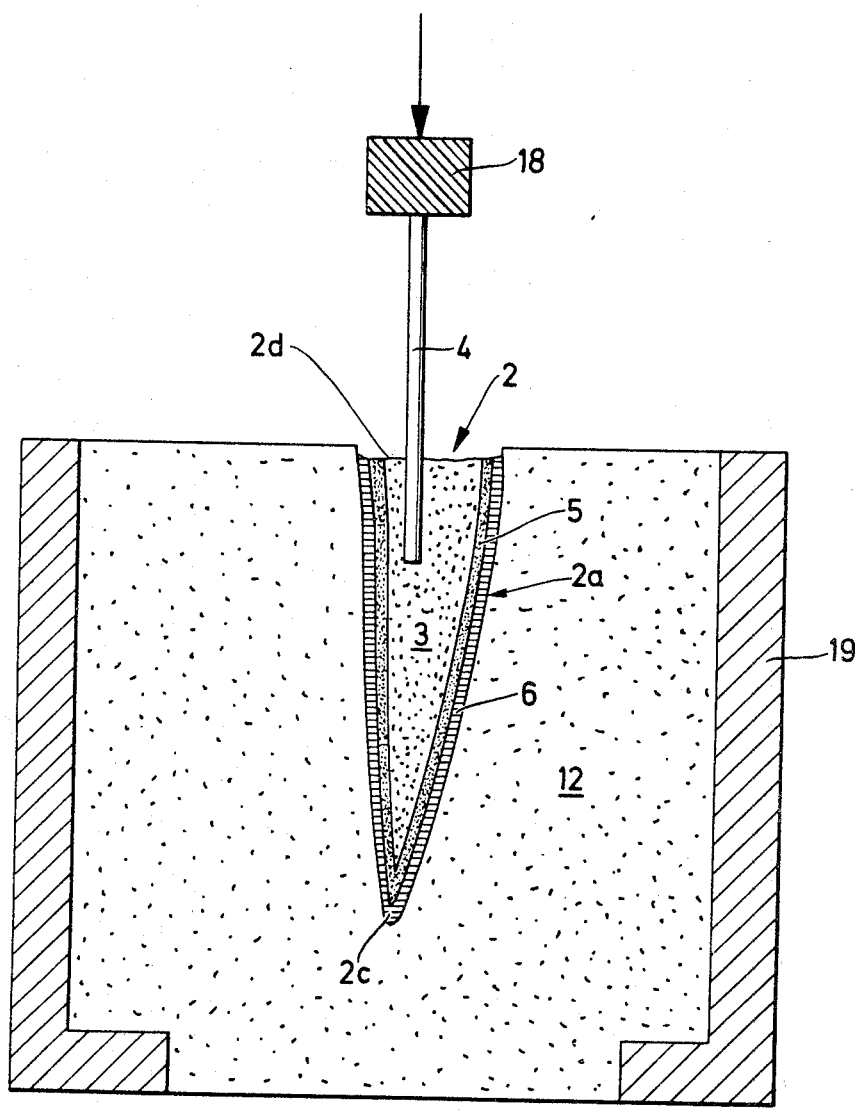
FIG. 2 shows the production of a dental root implant following a variation of the porcelain press technique according to the invention.

The techniques represented in FIGS. 1-3 are primarily intended for the production of implants which reproduce the extracted teeth or the extracted roots true to shape. These implants should in the root region be provided with a coating layer made from the ceramic substances according to the invention, this coating layer having a large number of vacuoles enabling tissue ingrowth and thus a rigid support. The technique described in FIG. 4 serves for making pressure-compacted ceramics containing no vacuoles, and will be discussed later.

The implants according to the invention are built up from different layers, these surrounding one another in a way similar to the dental prosthetic elements produced by conventional porcelain press techniques or metal-ceramic techniques.

FIG. 1 shows in the interior of a cuvette, which in connection with the porcelain press technique will be more closely dealt with later, an artificial tooth 1 according to the invention, in longitudinal section. In the case of this artificial tooth, crown and root are made as a single unit in one operation.

FIG. 2 shows likewise in the interior of a cuvette a dental root substitute 2, in transverse section, during the firing process at a point in time where a reinforcement element is just about to be introduced into the core area. The artificial tooth 1 and the dental root substitute 2 have the same layer-like constitution in the root region 2a. Seen from the inside to the outside they are made up of a core substance 3, in which a reinforcement element 4 is when necessary embedded. The core substance 3 is surrounded layerwise on the outside by a dentine substance 5, which in turn is surrounded by a layer 6 of the ceramic substance according to the invention. The layer 6 consists likewise of a dentine substance or core substance which according to the invention is mixed with thin inorganic fibers whose melting point is considerably higher than the temperature at which the materials making up the artificial tooth 1—or respectively the tooth substitution 2—are sintered. The layer 6, measuring preferably about 0.3 mm in thickness is, as already frequently described, permeated by a large number of vacuoles, these allowing ingrowth of bone tissue when the root region 2a is implanted in an artificial or natural tooth alveolus of the jaw.

In the examples illustrated it is assumed that the dentine substance in layers 5 and 6 is the same. For this reason the dividing line represented in the figure between these layer is, in a section through a real artificial tooth or a dental root substitute, only apparant in that within the dividing line there are no fibers, meaning that at the dividing line the porosity, or the depth of the vacuole-permeated outer layer, essentially ends.

In the case of the artificial tooth 1 represented in FIG. 1 the makeup of the crown region 7, this being constructed as a single entity with the root region 2a, differs from the makeup of the root region 2a only in that in place of the layer 6 from ceramic substances according to the invention, a layer 8, composed of a conventional enamel substance and in certain cases a layer 9 composed of a conventional transparent substance is deposited. Naturally the crown region 7 of the artificial tooth can be provided in familiar ways with additional substances responsible, for example, for colour effects, these helping to ensure that the artificial tooth optimally matches the neighbouring natural teeth. It is also possible to do without the layer 5 of dentine substance in the root region 2a, whereby in this case the ceramic base substance of the layer 6 can be made also from a core substance, instead of from a dentine substance. FIG. 3 shows the production of such an artificial tooth according to a variation of the press technique of the invention.

The artificial tooth 1 and the dental root substitute 2 can be made from metal-ceramic substances or from hard-porcelain substances, or from Vitadur- or Vitadur-S-substances, whereby corresponding core substances, corresponding dentine substances—also in layer 6—as well as corresponding enamel substances and corresponding transparent substances, i.e. enamel substances and transparent substances with corresponding thermal coefficients of expansion, are used. In the case of metal-ceramic substances the reinforcement element 4 consists of metal.

As metals in question here one can use, among other special alloys used in metal ceramics, gold alloys with a high platinum content, which for the purpose of increased hardness contain iron and other elements and melt at temperatures of about 1100°–1200° C. Also palladium alloys, hardened with ruthenium, with small amounts of gold or silver, which melt between about 1450° C. and 1600° C., as well as the so-called Feram alloys of cobalt-chrome from the Niranium Corporation Long Island, and D.J. metal with nickel as base material of the Durallium Products Co. Chicago. The DT-OS No. 25 14 672 describes further suitable alloys. Further examples of such alloys are known under the marks Degudent and Degucast, these being gold-ceramic and being manufactured by the firm Degussa GB Dental-und Goldhalbzeug D 6000 Frankfurt. Further gold-ceramics are known under the marks Herador (Firm Heraeus, V.4,V.44) (Firm Métaux Précieux) Degudent Swiss (Firm Cendres & Métaux) (Armator II) (Firm Usine Genevoise Degrossissage d'or) Williams Gold, Ceramco Gold and Stern Gold. From among the precious metal refined alloys are mentioned in particular Wiron S and Wiron, which have a composition on the basis of nickel-chrome and are manufactured by the firm Bremer Goldschlägerei Wilhm. Herbst 2800 Bremen 41.

In the case of hard-ceramic substances the reinforcement element 4 is a small hard-cement bar, tube or sheet, preferably of aluminium oxide.

Before describing in detail the special porcelain press technique according to the invention, as illustrated in FIGS. 1 and 2, it should be indicated that the artificial tooth and root according to the invention can also be made by normal methods involving free modelling based on a shape and layerwise firing. This method, with regard to procedure and in particular the firing temperatures used in each case does not differ from conventional ceramic techniques. It is not necessary at present to go into further detail, attention being drawn to familiar literature in this respect.

However, as opposed to the process by which the individual layers are freely modelled and fired on, the porcelain press technique according to the invention is preferable since with this it is possible, using molds of the natural tooth alveolus and/or with a mold of the extracted dental root or the extracted tooth, which, where necessary, can at defect points be correspondingly completed, to produce in a short time an artificial tooth or dental root substitute pertaining to the original in shape, and which for example can be completed and inserted into the tooth alveolus only a few hours after extraction of the tooth.

The porcelain press technique presented diagrammatically in FIG. 1 represents a further development of the porcelain press technique known as "Droege Technik". This familiar porcelain press technique is described for example in the journal "Zahnärztliche Welt/Rundschau" nr. 15,78 year 1969, pages 682–687, and in the journal "Das Dental Labor", issue 8/1976, as well as in the professional journal of the Swiss Zahntechniker-vereinigung "Die Zahntechnik", issue 1/1969, to which publications attention is hereby drawn. In these there are also examples of devices for the carrying out of such press procedures, especially cuvettes and furnaces. In the following these familiar porcelain press techniques will be dealt with only in so far as is necessary for understanding differences according to the invention.

FIG. 1 shows two cuvette halves 10 and 11 which are filled with an embedding substance 12. The embedding substance should if possible have a small thermal coefficient of expansion. Examples of embedding substances are special substances such as Deguvest from the firm Degussa GB Dental-und Goldhalbzeug D 6000 Frankfurt 1, Wirovest from the firm Bego, Bremer Goldschlägerei, Wilh. Herbst, 2800 Bremen 41, Emil-Sommer-Str. 7, Neo-Brillat from the firm Dentalchemie C. C. Schrepfer, Marburg/Lahn, Germany, Aurovest or Aurovest B, a quarz embedding substance from the firm Bego, Bremer Goldschlägerei, Wilh. Herbst and Hüdrovest from the firm Frankonia in Germany. In the embedding substance of the lower cuvette half, before it hardens, a wax model true to the original is embedded with the labial or lingual side down. Care is here taken that the root end 2c points towards an outlet 13 positioned at the edge of the cuvette half 11; a casting canal-like groove is introduced in the embedding substance from the root end 2c to the outlet 13, this being effected preferably by cutting it out from the hardened embedding substance. It is however also possible to insert a wax strip corresponding to the casting groove in the embedding substance before it hardens.

After hardening of the embedding substance in the lower cuvette half 11, a corresponding opposing mold is made in the upper cuvette half. Finally the wax model is scalded out, if necessary also the wax that fills the groove leading to the outlet 13. Instead of, or in addition to, the groove leading to the outlet 13 a further correspondingly-formed groove 20 can be provided, this leading from the crown region 7 to an outlet 21 positioned in the cuvette half 11. Should the groove 20—as later more clearly described—serve for the introduction of the reinforcement element 4, then it should run preferably as an axial extension to the artificial tooth 1.

In the cavities produced in this way in the cuvette halves 10 and 11 the porcelain substances are finally deposited layer-wise according to familiar methods, whereby in the root region 2a a layer of the ceramic substance according to the invention is deposited on the wall of the cuvette, and in the crown region a layer 9 of transparent material and a layer 8 of enamel. By means of intense kneading or by ultrasonics the substance, formed to a dough-like mass with water or corresponding mixing liquid, is compacted. The same applies for the subsequently deposited layer 5 of a dentine substance and the next deposited layer of a core substance. In order to compensate for the shrinkage caused by firing the substances are deposited in such a quantity that they mound up over the top edge of the cuvette. The reinforcement element 4 can be additionally inserted into the core substance.

Firing of the artificial tooth follows according to familiar methods, so that it is here unnecessary to go into further detail. As soon as an adequate firing temperature is reached the cuvettes are positioned and pressed against one another, so that the material in the two cuvette halves 10 and 11 sinter together to the uniform artificial tooth 1. The overflow of ceramic substance flows out through groove 14 leading from the dental root 2c to the outlet 13, and/or groove 20, which were not filled during the charging of the cuvette with embedding material, as indicated by the number 15. In this way a pressure build-up between the cuvette walls and the outermost layer of the artificial tooth which is greater than the pressure required for a normal sintering together of the substances is avoided. Too high a pressure would lead to the vacuoles which form in the ceramic substance according to the invention in the root region 2a being to a greater or lesser extent compressed.

To the left end of the cuvette half 11, when viewed in FIG. 1, an elbow is attached, which is positioned with its free end 16a reaching upwards free from, and longitudinal to the wall of the cuvette 11. There is a cylinder located in the free end 16a of the elbow 16 opposite the outlet 13, whose diameter corresponds approximately to the exterior diameter of a hard porcelain rod or tube 4a, so that this $Al_2O_3$ can be axially led into the cylinder 17. This construction enables the reinforcement element 4 to be pushed into the interior of the artificial tooth 1 by means of a plunger 18. In this case, after the sintering temperature has been reached, the rod 4a, shown in shortened form in FIG. 1, is pushed by means of the plunger 18 according to FIG. 1 so far to the right that its front end is lying approximately in the position indicated by the right-hand end of the reinforcement element 4, according to FIG. 1. The lumen of the opening 13 and the groove 14 are so selected as to allow overflow material 15 to flow easily past the inserted rod. When instead of the artificial tooth 1 a cast molded from the ceramic substances according to the invention should be fired, where the ceramic substances in this case are pressure-compacted in order to avoid the presence of vacuoles and to impart optimal rigidity to the body, then the procedure is as previously described, whereby in this case the lumen of the outlet 13 and the groove 14 are simply chosen to be so narrow that little or no material can squeeze out when the rod 4a is pushed in by the plunger 18. The groove 20 and the outlet 21 are in this case closed.

FIG. 2 shows a variation of the previously-described porcelain press technique according to the invention, whereby one makes do with a mold or cuvette 19 into whose embedding substance 12 a model of the dental root substance 2 is introduced complete, the root end 2c facing downwards. The material is introduced into the mold using corresponding methods as previously described by means of FIG. 1. The necessary compression during firing is achieved by putting the complete firing chamber 19, containing the cuvette, under excess pressure, when necessary also using gas an inert gas.

The tooth root substitute 2 represented in FIG. 2 is also reinforced in the core substance by pressing in a corresponding reinforcement element 4. If the reinforcement element 4 is sufficiently thick it is unnecessary to put the firing chamber under pressure since then an adequate compression is achieved by the pressing in of the reinforcement element. While in the procedure according to FIG. 1, where the rod or tube 4a is later pressed into the core substance, the end of the rod protruding beyond the root end 2c and the overflow material likewise accumulating here must be removed after completion of the artificial tooth, the free end of the reinforcement element 4 protruding upwards above the surface 2d of the dental root substitute 2 can serve as a mount for the crown put on later and also as a temporary fastening and support for the implanted dental root substitute onto the neighbouring teeth.

FIG. 3 shows a further stage of the porcelain press technique of FIG. 2. The embedding material 12 in the cuvette 25 forms, as in FIG. 2, a corresponding negative mold of the dental root substitute to be made. This negative mold is lined with a layer 26 of the ceramic substance according to the invention, which after the firing should form the porous outer layer and which is composed of a dentine- or core substance mixed with the inorganic fibers. The remaining interior space of the mold is filled with a dentine- or core substance 3. As indicated by the dash-dot line 27 an attachment 28 is fixed to the cuvette, this containing two concentric cylinders 29 and 30. The narrower of the two cylinders, 30, has its lower end opening out into the cast. A reinforcement element 24, whose outer diameter corresponds to the inner diameter of the cylinder 30, in the given case being a hard porcelain or metal tube closed at its lower end, is, as shown in FIG. 3, pushed down by a plunger 31 introduced into the larger cylinder 29, into the dentine- or core substance when this has sintered, this being indicated by a thermo-detecting element 33 attached on the bottom of the cuvette.

A pressure gauge 32 ensures that the force P pressing on the plunger 31 does not exceed a certain value. By means of corresponding alteration of this force the secondary compression of the sintered material in the cast is regulated and thereby also the porosity of the outer layer 26, depending on its fiber concentration.

The arrangement shown in FIG. 3 can also be used according to FIG. 4 for producing pressure-compacted casts, as for example the three-membered bride 36 as shown, which contains an outer layer of dentine, 34, and a core substance 35 mixed with fibers. The reinforcement element here not required is left out. Instead the core substance 35 fills out the cylinder 30 and the cylinder 29 below the plunger.

Before carrying out the press procedure in each case it is recommended to expose the cuvettes to a weak vacuum in order to remove any air bubbles present in the material, which could upset the quality of the end product.

For the production of dental root substitutes or artificial teeth pertaining to the original, a negative also true to the original is required, from which the dental root substitute or artificial tooth can be completed, as described above. The negative must be composed of an embedding substance which if possible has only a small thermal ability to expand. This shouldn't be greater than 1%.

The negative is made according to the invention as follows:

Before extracting the tooth or the dental root a complete impression of the jaw is made. This is followed by extraction of the tooth or the dental root. After correction of the gum edges, protruding gum being trimmed and flaps being cleared away, and where necessary after deepening the tooth recess by means of a bone cutter (mill), or a so-called "Rosenbohrer" or drill, and stopping the blood flow using a vessel-constricting substance, an elastic gum impression material is pressed into the tooth recess. By applying now the complete jaw impression which likewise in the region of the extracted tooth is filled with impression material, a "tooth or root positive" can in this way be obtained. After making plaster of Paris models the tooth positive which reproduces the root recess and the original crown true to shape can be built up to completion in the crown region according to the optimal gnathologic shape.

From the completed tooth positive, by constructing plaster of Paris models, the desired negative mold is then formed.

After firing and cooling of the artificial tooth or root, spills from excess material are removed. After covering the crown, for example with wax, the root region is further lightly treated with a sandblast blower, preferably with very fine silicon carbide, so that the pores of the substitute dental periosteum are opened. To the crown region of the artificial tooth a polish layer is also applied.

The entire process from the time of extraction can be carried out within three hours, so that after this time it is possible to implant the artificial tooth or the dental root in the tooth recess. In the meantime it is advisable to close off the alveolus by means of a folium adhering to the gum, or to fill it with a sterile tampon soaked with a bactericidal substance such as Merfen.

The implanted artificial tooth or dental root substitute is anchored to the neighbouring teeth until ingrowth of the bone tissue into the vacuoles is sufficient. Should for the moment only a dental root substitute be implanted, then this can be anchored by means of the free end of the rod 4a protruding at the top. It is however also possible to provide the dental root with a cylinder into which a pin from a supporting construction connected to the neighbouring teeth is inserted. The attachment of the implant to the neighbouring teeth can be removed again at the earliest after 6 weeks, as by this time the implant has been sufficiently penetrated by bone substance and can carry a normal load. An implanted dental root substitution is provided with the corresponding crown also at this time, this being done according to conventional methods.

Above, the invention has been described on the basis of dental implants pertaining to original shape. It is however clear that also pre-finished prosthetic elements can be produced according to the invention, these containing the ceramic substances according to the invention as the outer layer and/or in the case of using pressure-compacted substances, as reinforcement.

These elements can also be inserted into a toothless jaw, corresponding holes being prepared for this, preferably with a suitable and standardized bone mill. It is also possible to sew over the implanted roots with the mucous membrane periostal flaps. Otherwise the implant must be fixed by strutting with the teeth still present.

In addition attention is drawn to a further variation of the invention at hand, namely to produce, in shape pertaining to the original, an artificial tooth or dental root substitute from conventional dental-ceramic substances, especially metal-ceramic or hard porcelain substances, and in the dental root region, for example by means of a sandblast blower, to a thin layer onto which finally a ceramic substance according to the invention is fired, so that the dental root is provided with a layer permeated by vacuoles as periosteum substitute. Since the base material for the ceramic substance according to the invention can in this case be the same as the underlying layer, the firing of the ceramic substances according to the invention is completely problem-free, so that an intimate and firm binding is achieved without having to fear flaking or chipping.

In the following, supplementary to the description, some examples for the construction of implants according to the invention are given.

EXAMPLE 1

A Biodent-VMK base substance from the firm Detrey, which has been mixed to a paste with distilled water, is freely applied to a Wiron pin having a diameter of 3 mm and a thickness of about 1 mm, is pre-dried in the oven at about 500° C. for six minutes and is subsequently heated to 1020° C. and baked at this temperature for a length of about 6 minutes. After cooling a Biodent-VMK dentine substance which has been mixed to a paste with distilled water, is applied in a thickness of about 1 mm onto the Wiron pin with the base substance fired onto it and is pre-dried in the oven at about 500° C. for 6 minutes and then fired at about 930° C. for another 6 minutes.

A quantity of $\beta$-silicon carbide whiskers having a thickness of about 0.6 $\mu$m and lengths of approx. 1.5 mm is then weighed out, which, relative to a pre-prepared quantity of Biodent-VMK dentine substance accounts for 0.2 wt.%. The $\beta$-silicon carbide whiskers are suspended in about 50 wt.% glycerine, relative to the quantity of pre-prepared Biodent-dentine substance, in a petri dish. After suspending the carbide whiskers in glycerine the pre-prepared Biodent-VMK dentine substance is mixed in. The resulting substance is then heated at a temperature above the boiling temperature of glycerine long enough for all the glycerine to evaporate. A product in the form of dry powder is obtained, which is mixed to a paste with distilled water in the usual way and is applied to the Wiron pin in a thickness of about 0.5 mm, the pin having already had the Biodent-base substance and the Biodent-dentine substance fired onto it. The product is then pre-dried in the oven for 6 minutes at a temperature of about 500° C. and finally fired at a temperature of 930° C. for 6 minutes.

After cooling the product is carefully sandblasted whereby the vacuoles formed are opened. In the outermost layer the product contains about 70 vol.% vacuoles which for the most part exhibit a diameter of up to 200 $\mu$m.

EXAMPLE 2

Onto a Wiron pin, which has been treated according to example 1 with a layer of Biodent-VMK base substance and a layer of Biodent-VMK dentine substance, a ceramic substance according to the invention is applied corresponding to example 1, this substance differing from that in example 1 only in that the admixture of $\beta$-silicon carbide whiskers to the Biodent dentine substance accounts for about 0.5 wt.%.

The resulting products exhibit a surface permeated with vacuoles which is however a little bit denser, more brittle and with smaller pores than that from example 1. The pores have for the most part a diameter of up to 100 $\mu$m and account for about 65 vol. % of the outermost layer.

EXAMPLE 3

$\beta$-silicon carbide whiskers are weighed out in a quantity which accounts for about 0.15 wt.% of a pre-prepared Biodent-dentine-VMK substance. The whiskers are stirred into 30 wt.% heated cocoa butter, relative to the dry weight of the Biodent-dentine-VMK substance. The pre-prepared quantity of Biodent-dentine-VMK substance is then added. The paste produced in this way is applied to a Wiron pin which according to example 1 has been treated with both a layer of Biodent base substance and a layer of Biodent dentine substance. The pin is then pre-dried in an oven at about 500° C. for 6 minutes whereby the cocoa butter sublimes, is then fired at about 930° C. for 6 minutes and is then further processed according to example 1. The resulting product exhibits in the last-applied layer about 80 vol.% vacuoles, with diameters for the most part of up to 200 μm and a good rigidity. Under "good rigidity" one should understand from this disclosure that the pores are not pressed together when a sharp-edged metal object is manually pressed against some of the material also being held in the hand, and that scratching of the material manually using a sharp metal object is not possible.

EXAMPLE 4

The experiment from example 3 is repeated with a ceramic substance according to the invention, this having 0.01 wt.% β-silicon carbide whisker relative to the dry weight of the Biodent-dentine substance. The vacuole formation and the rigidity correspond approximately to that of the products obtained from example 3.

EXAMPLE 5

(a) A Vitadur dentine substance is mixed with about 0.1 wt.% basalt fibers having a diameter of about 6 um and lengths from about 1 mm. This mixture is mixed to a paste with about 10 wt.% heated cocoa butter. The substance so formed is applied in a thickness of about 400 μm to the walls of of a dental root negative which has been made in a Neo-Brillat embedding substance. In the region where the tooth root cuts through the jaw bone an approximately 2 mm-wide ring is carefully freed again.

(b) A Vitadur-dentine substance is mixed with 30 wt.% silver nitrate, then mixed together with a photo-developer (Dürr Sezialentwickler für Röntgenfilme in Röntgenentwicklungsmaschinen from the firm Dürr, D 7120 Bittigheim, West Germany)—to effect precipitatation of the silver as finely-divided metallic silver—and then dried and also ground. The dried product was mixed to a dough-like paste with about 10 wt.% cocoa butter and applied onto the cleaned area where the root cuts through in the dental root negative, with a thickness of about 400 μm.

(c) At a temperature of about 500° C. the dental root negative, with its wall lined as according to (a) and (b), is de-gased, until the porcelain substance, being black at first, has taken on a white colouring.

(d) The furnace is then brought to a temperature of about 920° C. The porcelain substance is baked for 10 minutes at this temperature.

(e) After cooling to hand warmth the dental root core is filled with a Vitadur core substance which has been made to a dough in the normal way with modelling liquid.

(f) At a temperature of 1020° C. the substance is fired according to FIG. 3 for 10 minutes.

(g) Subsequently a hard porcelain rod of $Al_2O_3$ is pressed by means of the plunger into the porcelain-filled cavity of the dental root negative from the crown part-pressure about 0.1 kp/cm². The oven is hereupon switched off.

(h) After cooling below 700° C. the cuvette is taken out of the furnace.

(i) When cold the artificial dental root is dis-embedded, cleaned and fitted into the Plaster of Paris model of the dentition and the tooth alveolus.

(j) The dental root is then carefully smoothed with a sheet of diamond and very carefully sandblasted. The vacuoles formed are in this way opened. The diameter of the vacuoles measures some 20–300 μm, larger vacuoles being present to the degree of less than 5%. The volume of vacuoles in the porous layer accounts for about 35%.

(k) After sterilizing, the dental root is implanted and remains attached to the neighbouring teeth for a period of 6 weeks.

(The silver layer applied in the region of the extrusion of the dental root through the jaw-bone is evident by X-Raying.)

EXAMPLE 6

The experiment of example 5 is repeated with regard to points (a)–(j), whereby however, instead of basalt fibers, 0.05 wt.% of carbon fibers are used, having a diameter of about 10 μm and lengths from about 0.5 to about 1.5 mm i.e. an average length of about 1 mm. The firing is carried out in a vacuum at about 10–20 mm Hg in order to prevent an oxidation of the carbon fibers. One obtains an implant having a firm surface permeated by relatively uniform vacuoles. The vacuoles have a diameter of about 50–300 μm whereby the vacuoles having a diameter larger than 300 μm are present to an extent of less than 2%. The number of very small vacuoles was also very small. The volume of vacuoles in the porous layer accounts for about 80%.

EXAMPLE 7

The experiment from example 6 is repeated with very good results using the same quantity (0.05 wt.%) β-silicon carbide whiskers, these having a length of about 1–2 mm and a diameter of about 6 μm. The vacuoles formed have a diameter of about 20–300 μm whereby vacuoles with a larger diameter are present to an extent of less than 3%. The volume of vacuoles in the porous layer accounts for about 75%.

The two following examples are concerned with the use of ceramic substances according to the invention for bone implants. A description is given for making bone substitute pieces which should replace in a long bone such as, for example, the thigh bone, a lengthwise piece destroyed by an explosion, crushing or suchlike. First of all by means of X-Rays the shape and extent of the missing piece of bone is determined and a corresponding wax model formed, this being provided at both its long ends with cone-like extensions, which reach into the cavity of the long bones at the two breakage points and which should strengthen the contact.

EXAMPLE 8

The wax model in a two-part cuvette according to FIG. 1 is so embedded in an embedding substance of Neo-Brillat, that the dividing line between both cuvettes extends approximately in the lengthwise direction of the bone substitute piece to be made, whereby an additional groove also running in a lengthwise direction parallel and between the cuvettes leading to the interior of the mold is formed, which enables the insertion of a hard ceramic core under pressure.

(b) The wax remainder is burned out at a temperature of about 500° C. The cuvette is then cooled to about 50° C.

(c) In the end regions of the two mold halves, into which a growing together of the bone substitute pieces with the respective bones should follow a 1 mm thick layer of a ceramic substance according to the invention is applied, its composition corresponding to the porous layer from example 6.

(d) The other wall regions of the mold halves are uniformly coated with an approximately 1 mm Vitadur-dentine layer, this likewise having been mixed to a paste with cocoa butter. These are particularly the lenthwise walls of the mold.

(e) The mold is then uniformly coated in a lengthwise direction with carbon fibers, these being orientated parallel to one another and if possible not overlapping, and being the same as those used in example 6. The lengths of the fibers correspond to the lengths of the bone substitute piece, so that they extend approximately from one end of the mold half to the other. In the example described they measure about 15 cm.

(f) Onto the carbon fibers in the mold a Vitadur base substance is applied in a thickness of some 0.3 mm, the Vitadur base substance having been mixed to a paste with cocoa butter. On top of this comes another layer of carbon fibers. This process is repeated until the thickness of the carbon fibers and the base substance layers lying one on top of the other is about 0.5 cm.

(g) The interior of the mold is then filled with a Vitadur base substance having been mixed to a paste with distilled water.

(h) The cuvette halves are pressed together and introduced into a furnace where the firing process is carried out under a vacuum of about 10–30 mm Hg. At first the body is dried over aperiod of about 2 hours at 600° C. The temperature is then raised to about 1020° C. As soon as it is determined that the interior of the cuvette i.e. that the ceramic substances heve reached this temperature, this being indicated by a thermometric guage placed in one of the cuvettes, the firing process is continued for a period of about 8 minutes.

(e) Subsequently, by means of the groove provided for this purpose, an aluminium oxide tube with external diameter of 8 mm and interior diameter of 3 mm is pressed in lengthwise direction and using a pressure of about 1 kp/cm$^2$ into the mold in such a way that it comes to lie along approximately the long axis of the bone substitute piece. The excess of the viscous base substance is hereby pressed into the interior of the tube.

(j) The furnace is then turned off. After half an hour the pressure in the oven is raised again to atmospheric pressure and the oven is opened. The mold remains in the oven until it has cooled to hand warmth.

(k) After removing the cuvette from the oven the cast is disembedded and cleaned.

(l) The surface regions, provided with a clean dentine layer, are polished and at 930° C. in the absence of a vacuum are exposed to a so-called gloss firing. The surface region covered with the substances according to the invention are then carefully smoothed with a sheet of diamond and very carefully sandblasted, so that the vacuoles formed there are opened. The vacuoles formed correspond approximately those of example 6.

(m) After trimming the broken bone ends the bone substitute piece is inserted operatively into the body. The affected body part is kept conventionally rested until the ingrowth of the bone tissue into the pores of the bone substitute piece is sufficient.

EXAMPLE 9

(a) A cast of Wiron is formed corresponding to the wax model.

(b) Onto the whole exterior surface of this Wiron body a Bioden-VMK base substance, having been mixed together with distilled water, is applied in a layer thickness of about 0.5 mm, pre-baked at 500° C. for about 30 minutes and after raising the temperature to 1020° C. is fired for about 15 minutes.

(c) Then, onto this, a layer of Biodent-VMK dentine substance is applied to a thickness of about 0.5 mm, the Biodent VMK substance having previously been mixed to a paste with distilled water, pre-baked at 500° C. for about 30 minutes and after raising the temperature to 1020° C. fired for about 15 minutes.

(d) Onto the end regions where an ingrowth of bone tissue should occur, a layer of ceramic substance according to the invention is applied to a thickness of about 1 mm, this substance having a composition corresponding to that of example 3, and is fired according to the method there described.

(e) The after-treatment of the resulting product is according to example 8. The vacuoles formed in the end regions correspond approximately to those in example 4.

I claim:

1. A dental implant wherein the surface portion thereof where tissue ingrowth is to occur is sintered and porous and comprises a biocompatible dental ceramic matrix containing about 0.02 to 0.05 wt. percent inorganic fibers having a diameter of less than about 0.6 mm and a length of about 0.1 to 60 mm, said surface portion comprising pores of an average pore diameter of approximately 100 to 200 μm and said inorganic fibers having a melting temperature higher than the sintering temperature of said matrix.

2. The implant as claimed in claim 1, wherein said porous surface layer comprises pores of an average pore diameter of about 10 to 200 μm, wherein pores having a diameter of greater than 300 μm comprise no more than 10% of the pores and wherein the pores comprise about 10 to about 90% of the total volume of the porous layer.

3. The implant as claimed in claim 2, wherein the pores comprise about 20 to about 30% of the total volume of the porous layer.

4. The implant as claimed in claim 2, wherein the sintering temperature of the ceramic matrix is 900° to 1400° C. and the melting temperature of the fibers is at least 400° C. higher than the sintering temperature.

5. The implant as claimed in claim 1, wherein the inorganic fibers are selected from the group consisting of a metal, a tungsten core coated with a metal carbide or metal dioxide and a ceramic.

6. The implant as claimed in claim 1, wherein the inorganic fibers are selected from the group consisting of quartz, carbon, basalt, a metal, boron carbide, silicon carbide, titanium diboride, beryllium oxide, boron nitrite, aluminum oxide, kaolin, Mullite, zirconium dioxide, zirconium silicate, magnesium oxide, aluminum nitrite and silicon nitrite.

7. The implant as claimed in claim 1, wherein the inorganic fibers are a metal or metal alloy and are selected from the group consisting of steel, a nickel alloy, niobium, molybdenum, tungsten, chrome, cobalt, nickel, copper and silver.

8. The implant as claimed in claim 1, wherein the inorganic fibers are a ceramic and are selected from the group consisting of boron carbide, boron nitride, zirconium silicate, zirconium dioxide, aluminum oxide and Mullite.

9. The implant as claimed in claim 1, wherein the fibers are a tungsten core coated with a member selected from the group consisting of boron carbide, silicon carbide and titanium dioxide.

10. The implant as claimed in claim 1, wherein the fibers have a thickness of about 0.5 μm to about 100 μm.

11. The implant as claimed in claim 1, further comprising finely-divided silver.

12. The implant as claimed in claim 11, wherein the finely divided metallic silver is formed by mixing the ceramic matrix with silver nitrate and then stirring to a dough-like paste in the presence of a photographic developer, whereby the finely divided metallic silver precipitates.

13. The implant as claimed in claim 1, wherein said porous layer has a thickness of from about 0.1 mm to about 5 mm.

14. The implant as claimed in claim 11, wherein the inorganic fibers are a metal alloy.

15. The implant as claimed in claim 1, wherein the inorganic fibers are selected from the group consisting of beryllium oxide, boron carbide, graphite, magnesium oxide, aluminum nitrite, sapphire and silicon carbide.

* * * * *